(12) United States Patent
Hori et al.

(10) Patent No.: US 10,622,130 B2
(45) Date of Patent: Apr. 14, 2020

(54) SUPERCONDUCTING MAGNET AND MAGNETIC RESONANCE IMAGING APPARATUS

(71) Applicant: HITACHI, LTD., Tokyo (JP)

(72) Inventors: Chishin Hori, Tokyo (JP); Manabu Aoki, Tokyo (JP); Akihisa Miyazoe, Tokyo (JP); Yukinobu Imamura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1121 days.

(21) Appl. No.: 15/002,491

(22) Filed: Jan. 21, 2016

(65) Prior Publication Data

US 2016/0225504 A1 Aug. 4, 2016

(30) Foreign Application Priority Data

Jan. 30, 2015 (JP) ................................. 2015-016285

(51) Int. Cl.
| | |
|---|---|
| *H01F 6/06* | (2006.01) |
| *G01R 33/38* | (2006.01) |
| *A61B 5/055* | (2006.01) |
| *H01F 6/04* | (2006.01) |
| *G01R 33/3815* | (2006.01) |

(52) U.S. Cl.
CPC ............. *H01F 6/06* (2013.01); *A61B 5/0555* (2013.01); *G01R 33/3804* (2013.01); *H01F 6/04* (2013.01); *G01R 33/3815* (2013.01)

(58) Field of Classification Search
CPC .............. A61B 5/0555; G01R 33/3804; G01R 33/3815; H01F 6/04; H01F 6/06
See application file for complete search history.

(56) References Cited

U.S. PATENT DOCUMENTS

| | | | | |
|---|---|---|---|---|
| 5,683,059 | A | * 11/1997 | Hara | ....................... B29C 70/08 174/125.1 |
| 2014/0357492 | A1 | * 12/2014 | Daibo | ....................... H01F 6/04 505/163 |

FOREIGN PATENT DOCUMENTS

JP 11-144940 A 5/1999

* cited by examiner

*Primary Examiner* — Bernard Rojas
(74) *Attorney, Agent, or Firm* — Mattingly & Malur, PC (57) ABSTRACT

A superconducting magnet in which efficiency of conduction cooling is improved is described as well as a magnetic resonance imaging apparatus that includes the superconducting magnet and requires no liquid helium. The magnet resonance imaging apparatus includes: a coil portion including a winding core, a winding portion formed by winding a wire around the winding core, a first flange provided on one side of the winding core, and a second flange provided on the other side of the winding core; a cooling device for cooling the coil portion; and a heat conducting member for thermally connecting the coil portion and the cooling device, in which at least one of the first flange, the second flange, and the winding core has a region made of a material whose thermal contraction rate is larger than a thermal contraction rate of the winding portion.

9 Claims, 5 Drawing Sheets

SUPERCONDUCTING MAGNET AND MAGNETIC RESONANCE IMAGING APPARATUS

TECHNICAL FIELD

The present invention relates to a superconducting magnet and a magnetic resonance imaging apparatus (hereinafter, referred to as an MRI apparatus) including the same.

BACKGROUND ART

An MRI apparatus can obtain an image indicating physical and chemical properties of a subject by placing the subject in an imaging space in which a uniform magnetostatic field is formed and using a nuclear magnetic resonance phenomenon occurring when the subject is irradiated with a radio frequency pulse. This image is mainly for medical use.

The MRI apparatus includes a magnetic device for forming a uniform magnetostatic field. A higher resolution image can be obtained as the magnetostatic field is larger. There are three kinds of magnets, i.e., a permanent magnet, a normal-conducting magnet, and a superconducting magnet. Among magnetic fields which can be generated by those magnets, the largest magnetic field is generated by the superconducting magnet. Therefore, currently, a major MRI apparatus generates a magnetostatic field with the use of a superconducting magnet.

The superconducting magnet includes a superconducting wire as a winding for allowing a current to pass therethrough. When the superconducting wire is cooled to have a certain temperature or less peculiar to a superconducting material, a current can flow through the superconducting wire with no resistance. Accordingly, it is possible to generate a large magnetic field by causing a large current to flow therethrough. Thus, the superconducting magnet needs to include a cooling mechanism for cooling a winding portion to maintain a low temperature state.

As a method for cooling a superconducting magnet, there is widely used a liquid helium immersion cooling in which a winding portion is immersed and is cooled in liquid helium. There is also widely used conduction cooling in which a chiller and a bobbin in which a coil is provided are connected by a heat transfer member made of a good heat conductor such as pure aluminum or oxygen-free copper and a superconducting magnet is cooled by the chiller via the heat transfer member. An advantage of the conduction cooling is that liquid helium serving as a coolant is not necessary. Because drain on a liquid helium resource has attracted attention all over the world in recent years, the above advantage of the conduction cooling is valued.

As a method for performing the conduction cooling on a superconducting magnet, Patent Literature 1 discloses a method for providing a heat transfer path by connecting a good heat conductor made of copper or the like to a bobbin made of stainless steel and connecting the good heat conductor to a chiller.

CITATION LIST

Patent Literature

PTL 1: JP-A-11-144940

SUMMARY OF INVENTION

Technical Problems

In the case where a superconducting magnet is subjected to conduction cooling, how to provide a heat transfer path for thermally connecting a chiller and a winding portion is important to quickly cool the superconducting magnet to a target temperature. In the method of Patent Literature 1, a winding portion is in thermal contact with the bobbin made of stainless steel and the bobbin is in contact with the heat transfer member made of the good heat conductor. Therefore, the heat transfer path for connecting the winding portion and the chiller is formed by connecting the bobbin and the heat transfer member in series, and conduction cooling is performed by the chiller via the heat transfer path. For example, assuming that the heat transfer member is metal having high purity, such as pure aluminum or oxygen-free copper, thermal conductivity is several hundreds of W/Km or more. Meanwhile, a stainless steel material has thermal conductivity of approximately several tens of W/Km. Therefore, the stainless steel material is not an excellent material as the heat transfer path. Further, in order to increase speed at which the winding portion is cooled via the bobbin, a contact area between the bobbin and the winding portion is important. The cooling speed is generally in proportion to a size of the contact area. When considering the contact area, a thermal contraction rate of each member is important. Although the superconducting magnet is produced at a normal temperature of approximately 300 K, the superconducting magnet is operated at a low temperature of approximately several K to several tends of K. Therefore, a size of each member is changed from the size thereof at a normal temperature. Accordingly, in terms of cooling efficiency, it is preferable to always maintain the contact area between the bobbin and the winding portion until a normal temperature at which cooling is started reaches a target cooling temperature. In the case where the contact area is decreased, the normal temperature cannot reach the target cooling temperature in some cases. Meanwhile, the winding portion is generally formed of resin. This is to prevent a superconducting wire from being deformed by large electromagnetic force applied to the superconducting wire when a large current flows and to fill a gap in the winding portion to improve thermal conductivity of the winding portion. However, because a thermal contraction rate of resin is several times higher than that of metal, a gap may be generated between the bobbin and the winding portion when resin is cooled to have a low temperature. This gap is not preferable when the winding portion is cooled by conduction cooling via the bobbin.

In view of this, objects of the present invention are to provide a superconducting magnet in which efficiency of conduction cooling is improved by securing the contact area between the winding portion and a member which is in contact therewith from a normal temperature to a low temperature and to provide a magnetic resonance imaging apparatus that includes the superconducting magnet and requires no liquid helium.

Solution to Problems

In order to achieve the above objects, for example, configurations described in Claims are adopted.

A conduction cooling superconducting magnet of the present invention includes: a coil portion including a winding core, a winding portion formed by winding a wire around the winding core, a first flange provided on one side of the winding core, and a second flange provided on the other side of the winding core; a cooling device for cooling the coil portion; and a heat conducting member for thermally connecting the coil portion and the cooling device, in which at least one of the first flange, the second flange, and the winding core has a region made of a material whose thermal contraction rate is larger than a thermal contraction rate of the winding portion.

Advantageous Effects of Invention

According to the present invention, it is possible to quickly cool a superconducting magnet. That is, a winding portion and a good heat conductor are directly in thermal contact with each other or a member for reducing a difference in thermal contraction absorbs a difference in thermal contraction between the winding portion and a portion from a winding core to a flange. Therefore, a thermal contact area between the good heat conductor and the winding portion is maintained from a normal temperature to a low temperature. This makes it possible to quickly cool the superconducting magnet.

DESCRIPTION OF EMBODIMENTS

In the following description, embodiments for implementing the present invention will be described with reference to drawings.

Embodiment 1

Figure 1:
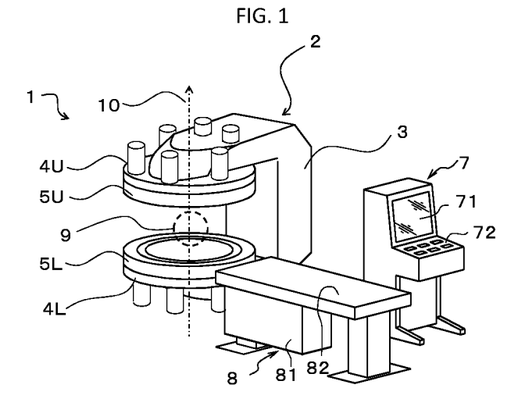
FIG. 1 is a perspective view of an MRI apparatus in Embodiment 1.

FIG. 1 is a perspective view of a magnetic resonance imaging apparatus 1 in Embodiment 1. As illustrated in FIG. 1, the magnetic resonance imaging apparatus 1 includes a magnetic device 2 for generating a uniform magnetic field in an imaging area 9, a bed 8 for carrying a test subject, i.e., a subject to the imaging area 9 while the subject is being laid, and a control unit 7 for controlling the whole magnetic resonance imaging apparatus 1 including the magnetic device 2, the bed 8, and the like. The magnetic resonance imaging apparatus 1 captures an MRI image indicating a physical property and a chemical property of the subject with the use of a nuclear magnetic resonance phenomenon generated when the subject positioned in the imaging area 9 in which the uniform magnetic field is formed is irradiated with a radio frequency pulse.

The control unit 7 is connected to the magnetic device 2 and the bed 8. The control unit 7 includes an operation unit 72 with which content of control is adjustable by operation performed by an operator and a display unit 71 for displaying a captured MRI image. The operation unit 72 receives the operation from the operator via a key, a rotary switch, or the like. The display unit 71 displays information on the operation received by the operation unit 72 and displays a captured MRI image. The control unit 7 receives various kinds of operation from the operator via the operation unit 72, controls the magnetic device 2 to generate a magnetic field on the basis of the operation, and controls the bed 8 to carry the test subject to the imaging area 9 in a horizontal direction.

The bed 8 includes a driving unit 81 provided in a lower part thereof and a top plate 82 which is horizontally moved by the driving unit 81 toward the imaging area 9. The test subject can lie on the top plate 82. The driving unit 81 moves the top plate 82 with the test subject mounted thereon and adjusts a position thereof to capture an MRI image of a desired part of the test subject.

The magnetic device 2 generates a uniform magnetic field in the imaging area 9. In the magnetic device 2, a pair of disk-shaped magnetic poles 4U and 4L are vertically arranged to face each other. The magnetic pole 4U and the magnetic pole 4L are made of iron, and rolled steel for general structure or the like is used. A material having higher magnetic permeability is desirable. A circular coil container 5U is adjacently arranged under the upper magnetic pole 4U. A circular coil container 5L is adjacently arranged on the lower magnetic pole 4L. The magnetic pole 4U and the magnetic pole 4L are supported by upper and lower projecting parts of an iron yoke 3. A central axis 10 passes through a center of the imaging area 9.

Figure 2:
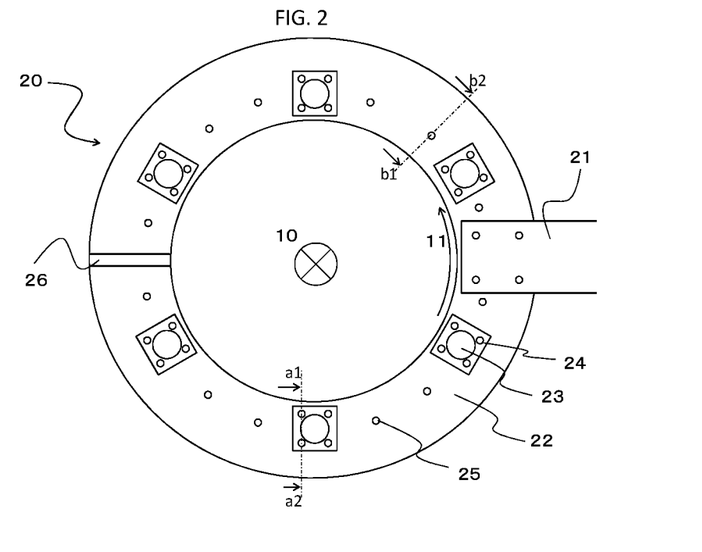
FIG. 2 is a diagram of a coil portion in Embodiment 1, seen from above in a coil axis direction.

FIG. 2 is a diagram of a coil portion 20 contained in the coil container 5U of a conduction cooling superconducting magnet which requires no liquid helium, seen from above in the central axis 10. A heat transfer member 21 thermally connects a chiller (not illustrated) which is a cooling device and a first flange 22. A load support 23 is connected to the coil portion 20 by a fastening member 24 so as to support the coil portion 20 on a side of the coil container 5U. The first flange 22 is made of a good heat conductor having large thermal conductivity, i.e., is made of pure metal such as copper or aluminum, and has a function of a heat transfer plate. Further, the first flange 22 is discontinuous in a coil circumferential direction 11 because of a slit 26. By providing the slit 26, there is decreased an amount of a magnetic flux penetrating a plane surrounded by an eddy current flowing through the first flange 22 when a value of a current flowing through a winding portion 28 is changed and a magnetic field is changed, and an induced voltage is decreased. Further, an electric resistance along a path of the eddy current is increased. Therefore, it is possible to reduce a magnitude of the eddy current and heat generation caused by the eddy current, as compared with a case of providing no slit 26.

Figure 3:
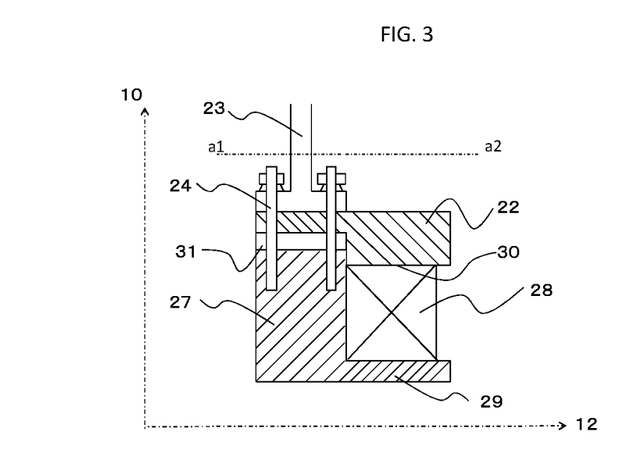
FIG. 3 is a cross-sectional view of the coil portion in Embodiment 1 which includes a load support.

FIG. 3 is a cross-sectional view of the coil portion 20 including the load support 23, taking along a cross-section a1a2. The load support 23 and a winding core 27 are connected by the fastening member 24 while interposing the first flange 22 therebetween. The first flange 22 and a second flange 29 are provided on both sides/both ends of the winding core 27 in the central axis direction 10. The winding core 27 is wound by a superconducting wire to form the winding portion 28. The winding portion 28 is supported by the first flange 22, the winding core 27, and the second flange 29. In this embodiment, the winding core 27 and the second flange 29 are integrally provided. In the case where the winding core 27 and the second flange 29 are made of the same material, by integrally forming the winding core 27 and the second flange 29, a thermal resistance between the winding core 27 and the second flange 29 is decreased, and cooling speed of the coil portion 20 is improved accordingly. The first flange 22 and the winding core 27 are different members and are connected by the fastening member 24. Similarly, the second flange 29 may be a member which is different from the winding core 27, is a heat transfer plate having high thermal conductivity, and is connected to the winding core 27 by a fastening member. The winding portion 28 is formed by resin transfer molding and a gap in the superconducting wire is filled with resin. With this, structural strength of the winding portion 28 is increased, and thermal conductivity of the winding portion 28 in the central axis direction 10 and a radial direction 12 is improved. Contact surfaces 30 between the first flange 22 and the winding portion 28 are adhered. As an adhesive, for example, an adhesive for a low temperature or epoxy resin is used. A thermal contraction difference absorbent material 31 is interposed between the first flange 22 and the winding core 27. The thermal contraction difference absorbent material 31 is interposed between the first flange 22 and the winding core 27 and assists the first flange 22 to move in the central axis direction 10 in accordance with thermal contraction of the winding portion 28. Further, the thermal contraction difference absorbent material 31 may be included in a lower part of the first flange 22 to function as a part thereof and may be formed to improve followability of move of the first flange 22 caused by thermal contraction in the central axis direction 10. Furthermore, the thermal contraction difference absorbent material 31 may be included as a part of the winding core 27 and may be formed to improve a degree to thermally contract the winding core 27 in the central axis direction 10.

A thermal contraction rate of the winding portion 28 depends on a superconducting wire to be used and the kind of resin. Generally, a thermal contraction rate of the superconducting wire largely influences the thermal contraction rate of the winding portion 28 in the coil circumferential direction 11, and a thermal contraction rate of resin largely influences the thermal contraction rate of the winding portion 28 in the central axis direction 10. For example, a thermal contraction rate of metal such as iron, copper, aluminum, and stainless steel at 20 K or less is approximately 0.2 to 0.4% of the thermal contraction rate at 290 K, whereas a thermal contraction rate of epoxy resin which is frequently used for resin transfer molding of the superconducting wire is 1% or more, which is 2 to 5 times thereof. Therefore, regardless of the kind of the superconducting wire, the thermal contraction rate of the winding portion 28 in the central axis direction 10 is approximately 2 or more times larger than that in the coil circumferential direction 11. Accordingly, in the case where the first flange is positioned above the second flange in the vertical direction, the contact surfaces 30 adhered at a normal temperature are separated by an amount corresponding to a difference between thermal contraction of the winding core 27 and the first flange 22 and thermal contraction of the winding portion 28 as the normal temperature is cooled to a low temperature. In this case, in the case where the thermal contraction difference absorbent material 31 is a member having a large thermal contraction rate, the thermal contraction difference absorbent material 31 absorbs the difference in the thermal contraction, and therefore the first flange 22 can follow contraction of the winding portion 28. This makes it possible to prevent separation of the contact surfaces 30. For example, in the case where the thermal contraction difference absorbent material 31 is made of polytetrafluoroethylene, the thermal contraction rate of the thermal contraction difference absorbent material 31 at 20 K or less is approximately 2% of the thermal contraction rate at 290 K. Therefore, the thermal contraction difference absorbent material 31 actually absorbs the difference in thermal contraction. A material of the first flange 22 is selected so that the difference in thermal contraction between the first flange 22 and the winding portion 28 is decreased in the coil circumferential direction 11 and the coil radial direction 12. For example, an oxygen-free copper plate is suitable for a niobium titanium wire which is the most common as the superconducting wire.

Heat referred to as alternating-current heat is generated in the winding portion 28 during excitation, and therefore a temperature thereof becomes higher than the temperature in a steady state achieved by cooling the temperature with the use of the chiller. At this time, in this embodiment, the winding portion 28 and the first flange 22 which is a good heat conductor are in direct contact with each other, and therefore it is possible to quickly remove heat from the winding portion 28 via the first flange.

Figure 4:
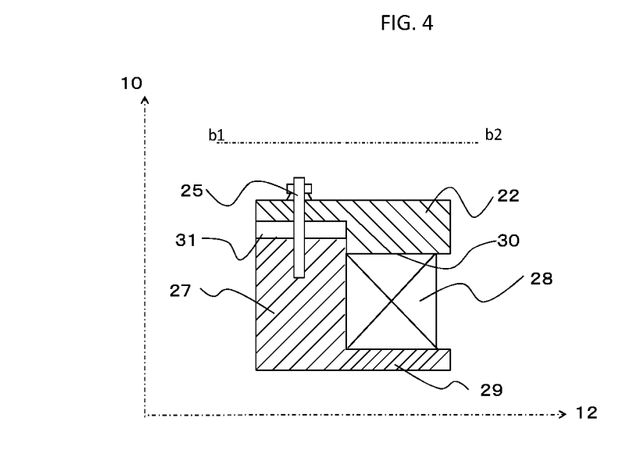
FIG. 4 is a cross-sectional view of the coil portion in Embodiment 1 which does not include the load support.

FIG. 4 is a cross-sectional view of the coil portion 20, taken along a cross-section b1b2. The first flange 22 and the winding core 27 are fastened by a fastening member 25, and the thermal contraction difference absorbent material 31 is interposed between the first flange 22 and the winding core 27.

In this embodiment, the first flange 22 functioning as a heat transfer plate is positioned above the second flange in the vertical direction, and, when the winding portion 28 is electrified, electromagnetic force acts on the winding portion 28 so that the winding portion 28 is attracted to the iron yoke 3 and moves upward in a vertical direction, i.e., upward in the coil axis direction 10. Such a direction of this electromagnetic force is a direction in which the first flange 22 and the winding portion 28 are press-bonded more securely. By arranging the heat transfer plate in a direction in which the winding portion 28 moves due to electromagnetic force as described above, it is possible to increase a thermal contact area at the time of electrification.

From the above, according to Embodiment 1, the thermal contraction difference absorbent material 31 absorbs the difference between the thermal contraction of the winding core 27 and the first flange 22 and the thermal contraction of the winding portion 28. Therefore, the contact surfaces between the first flange 22 and the winding portion 28 are not separated from the normal temperature to the low temperature, and thermal contact is maintained, with the result that the cooling speed is improved. Further, because the first flange 22 which is a good heat conductor and the winding portion 28 are in direct contact with each other, it is possible to quickly remove heat generated in the winding portion 28. Furthermore, because the first flange 22 also functions as the heat transfer plate and the electromagnetic force acts on the winding portion 28 in a direction in which the winding portion 28 moves upward in the coil axis direction 10 at the time of electrification, the contact area between the first flange 22 and the winding portion 28 is increased at the time of electrification, and therefore heat is easily removed from the winding portion 28.

In this embodiment, as the thermal contraction difference absorbent material 31 in the central axis direction 10, a material having a different thermal contraction rate from that of stainless steel which is a base material of the winding core 27 is partially used in the winding core 27. The thermal contraction difference absorbent material 31 is provided to occupy all/most of a cross-sectional area of the winding core 27, the cross-sectional area being perpendicular to the central axis direction 10. With this, contraction of the winding core 27 in the central axis direction 10, which is caused by a change in a temperature, can follow contraction of the winding portion 28, and the contact area between the winding portion 28 and the first flange 22 can be maintained. In that case, the above effects can be obtained regardless of where in the winding core 27 the thermal contraction difference absorbent material 31 is provided.

This embodiment has been described assuming that the side on which the load support 23 is connected is an upper side. However, effects of the present invention can be similarly obtained in the case where the load support 23 is supported on a lower side.

Note that, in this embodiment, an MRI superconducting magnet device for generating a magnetostatic field in the vertical direction has been described as an example. However, the present invention is applicable not only to an MRI superconducting magnet device for generating a magnetostatic field in the horizontal direction but also to a general conduction cooling superconducting magnet.

Further, as effects of an MRI apparatus in this embodiment, it is possible to reduce electricity consumption by improving cooling efficiency and is also possible to reduce a necessary capacity of the cooling device. Furthermore, it is possible to early start up the apparatus by improving the cooling speed.

Embodiment 2

Figure 5:
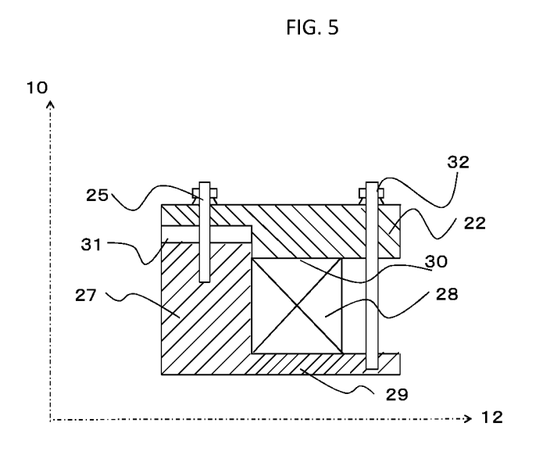
FIG. 5 is a cross-sectional view of a coil portion in Embodiment 2.

FIG. 5 is a cross-sectional view of a coil portion in Embodiment 2. Embodiment 2 is a modification example of Embodiment 1, and, in Embodiment 2, the first flange 22 and the second flange 29 are fastened by a circumferential fastening member 32 in addition to the structure of Embodiment 1. In this case, by selecting a material and a size of the second flange 29 so that the thermal contraction rate of the second flange 29 in the coil radial direction 12 is closer to the thermal contraction rate of the winding portion 28 in the coil radial direction 12 than to the thermal contraction rate of the first flange 22 in the coil radial direction 12 and rigidity of the second flange 29 is larger than that of the first flange 22, the second flange 29 corrects contraction of the first flange 22. This makes it possible to suppress a shift caused by thermal contraction of the first flange 22 and the winding portion 28 in the coil radial direction 12. Therefore, it is possible to select a material while a magnitude of the thermal conductivity is considered more important than making adjustment so that a material of the first flange 22 has the same thermal contraction rate as that of the winding portion 28. In the case where a position where the first flange 22 and the second flange 29 are fastened is outside a circumferential surface of the winding portion 28, a correction effect is improved.

From the above, not only in Embodiment 1 but also in Embodiment 2, the thermal contraction difference absorbent material 31 absorbs the difference between the thermal contraction of the winding core 27 and the first flange 22 and the thermal contraction of the winding portion 28. Therefore, the contact surfaces between the first flange 22 and the winding portion 28 are not separated from the normal temperature to the low temperature, and thermal contact is maintained, with the result that the cooling speed is improved. Further, because the first flange 22 which is a good heat conductor and the winding portion 28 are in direct contact with each other, it is possible to quickly remove heat generated in the winding portion 28. Furthermore, because the first flange 22 also functions as the heat transfer plate and the electromagnetic force acts on the winding portion 28 in a direction in which the winding portion 28 moves upward in the coil axis direction 10 at the time of electrification, the contact area between the first flange 22 and the winding portion 28 is increased at the time of electrification, and therefore heat is easily removed from the winding portion 28.

Embodiment 3

Figure 6:
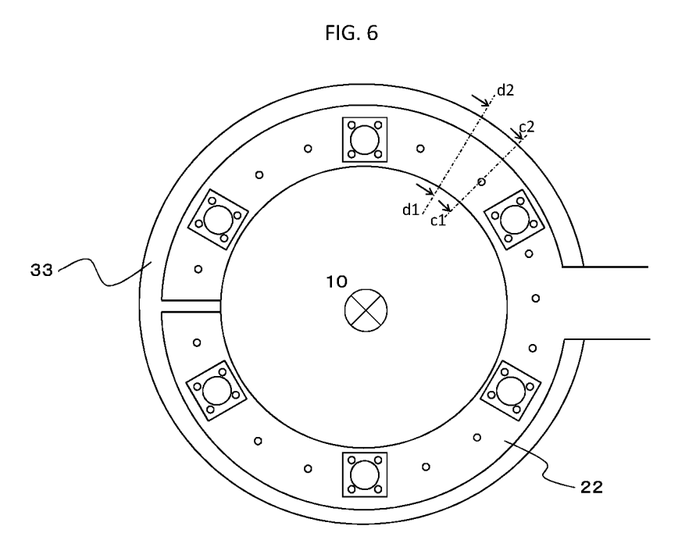
FIG. 6 is a diagram of a coil portion in Embodiment 3, seen from above in a coil axis direction.

FIG. 6 is a diagram of a coil portion of an MRI superconducting magnet in Embodiment 3, seen from above in the coil central axis direction 10. In this embodiment, the first flange includes a plurality of members such as two members, i.e., a first flange 33 and the first flange 22. In other words, the first flange includes a plurality of members such as the first flange 33 and the first flange 22. The first flange 22 is a heat transfer plate functioning as a good heat conductor and is connected to a chiller. The first flange 33 is a structural member made of stainless steel or the like and has electrical resistivity which is one hundred or more times higher than that of copper or aluminum having high purity. Therefore, there is no need to provide a slit as a countermeasure against an eddy current. Meanwhile, the first flange 22 having a function of the heat transfer plate has a slit in a coil circumferential direction as a countermeasure against an eddy current, as in Embodiment 1 and Embodiment 2.

Figure 7:
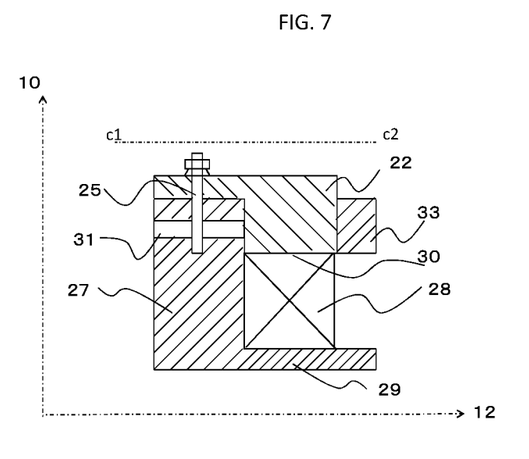
FIG. 7 is a cross-sectional view of the coil portion in Embodiment 3.

FIG. 7 is a cross-sectional view of a coil portion, taken along a cross-section c1c2. In the cross-section c1c2, the first flange 22 has an L shape and is fitted into a through hole of the first flange 33, and an L-shaped protruding portion of the first flange 22 penetrates the first flange 33 to be brought into contact with the winding portion 28. The contact surfaces 30 between the first flange 22 and the winding portion 28 are adhered to each other, as in Embodiment 1 and Embodiment 2. Further, the thermal contraction difference absorbent material 31 is interposed between the first flange 33 and the winding core 27.

Figure 8:
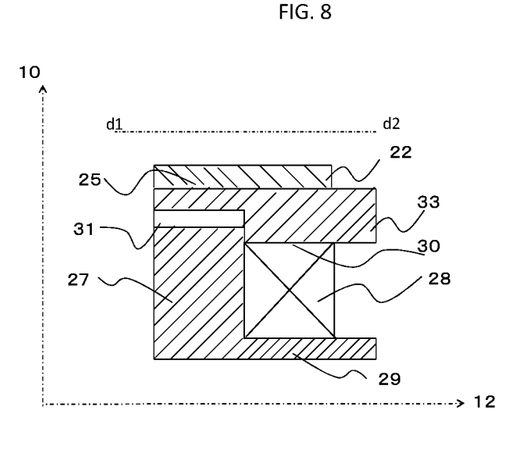
FIG. 8 is a cross-sectional view of the coil portion in Embodiment 3.

FIG. 8 is a cross-sectional view of a coil portion, taken along a cross-section d1d2. In the cross-section, the first flange 22 has a flat shape and the first flange 33 does not have a hole. Therefore, the first flange 22 is not directly brought into thermal contact with the winding portion 28.

Advantages of the shapes illustrated in FIG. 7 and FIG. 8 are as follows. First, the first flange 22 having the function of the heat transfer plate is in direct contact with the winding portion 28, the thermal contraction difference absorbent material 31 absorbs a difference between thermal contraction of the winding core 27, the first flange 22, and the first flange 33 and the thermal contraction of the winding 28. Therefore, as in Embodiment 1 and Embodiment 2, the contact surfaces between the first flange 22 and the winding portion 28 are not separated from the normal temperature to the low temperature, and thermal contact is maintained, with the result that the cooling speed is improved. Further, because the first flange 22 which is a good heat conductor and the winding portion 28 are in direct contact with each other, it is possible to quickly remove heat generated in the winding portion 28. Furthermore, because the first flange 22 also functions as the heat transfer plate and the electromagnetic force acts on the winding portion 28 in a direction in which the winding portion 28 moves upward in the coil axis direction at the time of electrification, contact between the first flange 22 and the winding portion 28 is increased at the time of electrification, and therefore heat generated in the winding portion 28 during electrification is easily removed.

Further, by selecting, as a material of the first flange 33, a material having a value closer to the thermal contraction rate of the winding portion 28 in the coil radial direction 12 than to the thermal contraction rate of the first flange 22 in the coil radial direction 12, it is possible to suppress the thermal contraction of the first flange 22 in the coil radial direction 12 and reduce the difference in thermal contraction between the first flange 22 and the winding portion 28 in the radial direction 12. With this, it is possible to select a material while a magnitude of the thermal conductivity is considered more important than making adjustment so that the first flange 22 has the same thermal contraction rate as that of the winding portion 28.

Figure 9:
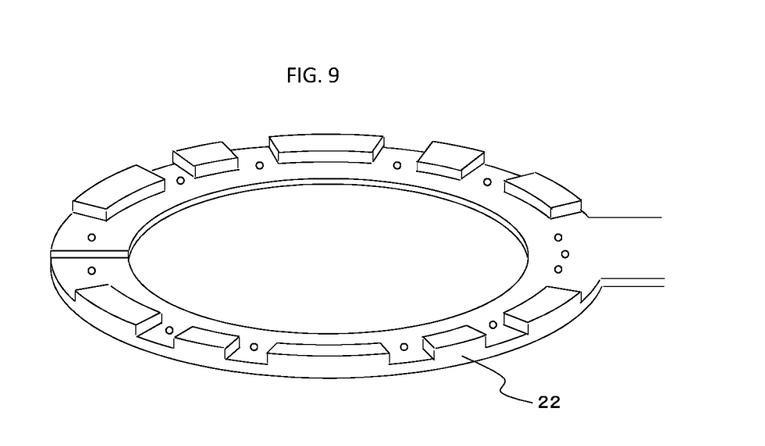
FIG. 9 is a diagram of a first flange of a coil portion in Embodiment 3, seen from below in a coil axis direction.

FIG. 9 is a diagram of the first flange 22 in this embodiment, seen from a back side. Portions which penetrate the first flange 33 and are in direct contact with the winding portion 28 project from a back surface of the first flange 22 to have a protruding shape, and those protruding portions are distributed in the circumferential direction of the first flange 22.

Embodiment 4

Figure 10:
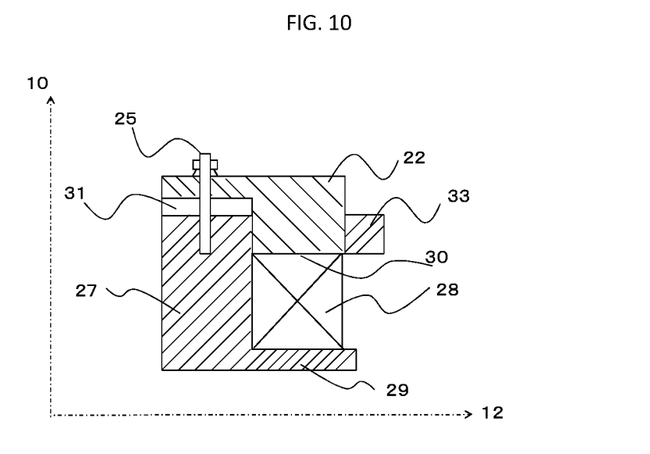
FIG. 10 is a cross-sectional view of the coil portion in Embodiment 4.

FIG. 10 is a cross-sectional view of a coil portion of an MRI superconducting magnet in Embodiment 4. This embodiment is a modification example of Embodiment 3. As compared with Embodiment 3, the winding core 27 and the first flange 33 are integrally provided and the thermal contraction difference absorbent material 31 is interposed between the first flange 22 and the winding core 27. In this embodiment, a structure of the first flange includes the first flange 33 and the first flange 22, a through hole is provided in the first flange 33, the first flange 22 is fitted into the through hole of the first flange 33, and the first flange 22 is in contact with the winding portion 28.

Advantages of this structure are as follows. In the case where a superconducting wire made of, for example, niobium-tin or magnesium diboride is used, in some cases, a coil is produced by a method referred to as Wind & React (hereinafter, W&R) in which a superconducting wire is wound around a winding core and is then subjected to heat processing. In this case, in the case where the coil portion 20 is made of pure aluminum or oxygen-free copper, a shape thereof is deformed because heat processing is performed at a high temperature of approximately 900 K or more. Therefore, in many cases, a stainless steel material is used as a structural material of the coil portion 20. However, in order to provide a conduction cooling superconducting magnet in which a coil portion is cooled by a chiller via a heat transfer path, a stainless steel material is not preferable because thermal conductivity thereof is 10 W/Km, i.e., is small. In this case, in the case where the first flange 33 and the thermal contraction difference absorbent material 31 are made of stainless steel, and, after heat processing, the first flange 33 is replaced with a first flange made of oxygen-free copper or pure aluminum and the thermal contraction difference absorbent member 31 is also replaced with an original member, it is possible to place the first flange 22 as a heat transfer plate that is in direct contact with the winding portion 28 with less coil portion disassembling steps while maintaining fixation of an upper part of the winding portion 28 with the use of the first flange 33. This makes it possible to quickly cool the coil produced by W&R to a low temperature by using conduction cooling.

REFERENCE SIGNS LIST 1 magnetic resonance imaging apparatus
2 magnetic device
3 iron yoke
4U, 4L magnetic pole
5U, 5L coil container
6U, 6L superconducting coil
7 control unit
8 bed
9 imaging area
10 coil central axis
11 coil circumferential direction
12 coil radial direction
21 heat transfer member
22 first flange
23 load support
24, 25 fastening member
26 slit
27 winding core
28 winding portion
29 second flange
30 contact surface
31 thermal contraction difference absorbent member
32 circumferential fastening member
33 first flange

The invention claimed is:

1. A superconducting magnet, comprising:
   a coil portion including a winding core, a winding portion formed by winding a wire around the winding core, a first flange provided on one side of the winding core, and a second flange provided on the other side of the winding core;
   a cooling device for cooling the coil portion; and
   a heat conducting member for thermally connecting the coil portion and the cooling device,
   wherein the first flange and the winding core are joined by a first fastening member with a thermal contraction difference absorbent member interposed between the winding core and the first flange,
   wherein the thermal contraction difference absorbent member has a thermal contraction rate in a coil central axis direction that is larger than a thermal contraction rate in the coil central axis direction of the winding portion.

2. The superconducting magnet according to claim 1, wherein
   the first flange is in contact with the winding core.

3. The superconducting magnet according to claim 1, wherein
   the second flange is integrally provided with the winding core.

4. The superconducting magnet according to claim 1, wherein
   the first flange and the second flange are fastened by a second fastening member outside a circumferential surface of the winding portion.

5. The superconducting magnet according to claim 1, wherein:
   the first flange includes a plurality of members;
   one of the plurality of members has a through hole;
   another one of the plurality of members has a protruding portion to be fitted into the through hole;
   the member having the protruding portion is connected to the heat conducting member;
   the member having the through hole, the member having the protruding portion, and the winding core are joined by the first fastening member with the thermal contraction difference absorbent member interposed between the winding core and the member having the through hole; and the protruding portion is in contact with the winding portion at a position further than the first fastening member in a coil radial direction.

6. The superconducting magnet according to claim 1, wherein:
the first flange includes a plurality of members;
one of the plurality of members is integrally provided with the winding core;
one of the plurality of members is integrally provided with the winding core and has a through hole;
another one of the plurality of members has a protruding portion to be fitted into the through hole;
the member having the protruding portion is connected to the heat conducting member;
the member having the protruding portion and the winding core are joined by the first fastening member with the thermal contraction difference absorbent member interposed between the winding core and the member having the protruding portion; and
the protruding portion is in contact with the winding portion at a position further than the first fastening member in a coil radial direction.

7. The superconducting magnet according to claim 1, wherein
a material of the first flange is one of oxygen-free copper, pure aluminum, or pure iron; and
the first flange is discontinuous in a coil circumferential direction.

8. The superconducting magnet according to claim 1, wherein
contact surfaces between the winding portion and the first flange are adhered to each other via an adhesive or resin at a position further than the first fastening member in a coil radial direction.

9. A magnetic resonance imaging apparatus, comprising:
a bed for carrying a subject to an imaging area;
a magnetic device for generating a uniform magnetic field in the imaging area; and
a control unit for controlling the bed and the magnetic device,
wherein the magnetic device is the superconducting magnet according to claim 1.

* * * * *